(12) United States Patent
Carter et al.

(10) Patent No.: US 8,354,116 B2
(45) Date of Patent: Jan. 15, 2013

(54) BIFUNCTIONAL SYNTHETIC MOLECULES

(75) Inventors: Stephen G. Carter, Andover, MA (US); Kanu Patel, Londonderry, NH (US); Zhen Zhu, Tewksbury, MA (US); Lixin Qiao, Tewksbury, MA (US)

(73) Assignee: BioChemics, Inc., Danvers, MA (US)

( * ) Notice: Subject to any disclaimer, the term of this patent is extended or adjusted under 35 U.S.C. 154(b) by 1247 days.

(21) Appl. No.: 11/820,172

(22) Filed: Jun. 18, 2007

(65) Prior Publication Data

US 2008/0312296 A1    Dec. 18, 2008

(51) Int. Cl.
*A61K 9/00* (2006.01)
*A61K 8/02* (2006.01)

(52) U.S. Cl. .................. 424/400; 424/401

(58) Field of Classification Search .............. None
See application file for complete search history.

(56) References Cited

U.S. PATENT DOCUMENTS

| | | | | |
|---|---|---|---|---|
| 4,555,398 A * | 11/1985 | Oda | | 514/307 |
| 5,460,821 A | 10/1995 | Masiz | | 424/449 |
| 5,645,854 A | 7/1997 | Masiz | | 424/449 |
| 5,853,751 A | 12/1998 | Masiz | | 424/449 |
| 6,019,997 A * | 2/2000 | Scholz et al. | | 424/449 |
| 6,372,712 B1 * | 4/2002 | Briesewitz et al. | | 514/20.9 |
| 6,635,274 B1 | 10/2003 | Masiz | | 424/449 |

FOREIGN PATENT DOCUMENTS

CA    2360590 A1    4/2002

OTHER PUBLICATIONS

Lai et al. Structural Characteristics of Human Erythropoietin, Mar. 5, 1986, The Journal of Biological Chemistry, 3116-3121.*

Chinese Office Action, with English translation, dated Apr. 20, 2011 in corresponding foreign patent application No. CN 200880103516.1.
Wang, Xiu Q., et al., "Erythropoietin Depresses Nitric Oxide Synthase Expression by Human Endothelial Cells", Hypertension. 1999, 33:894-899.
Krapf, Reto, et al., "Arterial Hypertension Induced by Erythropoietin and Erythropoiesis-Stimulating Agents (ESA)", Clinical Journal of the American Society of Nephrology, Feb. 2009, vol. 4 No. 2, pp. 470-480 + refs.
Canadian Communication dated Mar. 8, 2012 in corresponding Canadian patent application No. CA 2690357.
Canadian Communication dated Jul. 25, 2011 in corresponding Canadian patent application No. CA 2690357.
Chinese Communication, with English translation, dated Mar. 28, 2012 in corresponding Chinese Patent Application No. 2008801035161, 11 pages.

* cited by examiner

*Primary Examiner* — Robert A Wax
*Assistant Examiner* — Melissa Mercier
(74) *Attorney, Agent, or Firm* — Nields, Lemack & Frame, LLC

(57) ABSTRACT

The synthesis and use of bifunctional molecules to improve the topical and transdermal delivery efficiency of various types of therapeutic agents or agents designed to promote the transdermal delivery of those therapeutic agents either into the skin tissue or into the systemic circulation. Three major classes of molecules are covalently joined as bifunctional substances; chemical vasodilators, passive dermal penetration enhancers and therapeutic or diagnostic drugs. Chemical vasodilators may be delivered into the skin to increasing the blood flow in a tissue that has compromised circulation or they may be used as part of a delivery vehicle to promote the delivery of the drug. Passive dermal penetration enhancers are those chemicals that promote the passive penetration of drugs and other chemicals through the stratum corneum and epidermis of the skin tissue. Drugs and diagnostic agents are the third group of chemicals that are candidates for the linkage of molecules.

4 Claims, No Drawings

007
BIFUNCTIONAL SYNTHETIC MOLECULES

BACKGROUND OF THE INVENTION

The current invention describes the preparation of a novel series of chemically bifunctional function molecules with the design purpose of improving the pharmacologic characteristics of either the vasodilator or the drug/diagnostic moiety. There are published reports suggesting that in many medical conditions related to peripheral vascular disease and neuropathy, including diabetic neuropathy, there is a compromised microcirculatory environment around the nerves, which may have an influence on the normal functions of the nerves, leading to the abnormal sensations or lack of sensations noted with these medical conditions. Improving the metabolic state in the tissue around the nerve cells in the skin through an improved blood flow, increasing the oxygenation and nutrient delivery to the tissue as well as improving the removal of cellular and tissue waste products, improves the health and functioning of the nerve cells, which in turn creates an environment for the reversal of a deteriorating medical condition or slows the rate of deterioration. The use of bifunctional function molecules, including the use of vasodilators linked to a penetration enhancer molecule would improve the delivery of these agents to the compromised tissue.

The preparation of the stable and covalently linked bifunctional molecules from components such as a vasodilator (e.g., nicotinic acid or tolazoline) linked to a penetration enhancing moiety (e.g., menthol or linoleic acid), allows for the more efficient and coordinated delivery of the active agents (i.e., drugs or vasodilators). The improved delivery of a functional drug agent or vasodilator improves the treatment of a medical condition in a manner that can be more accurately measured and predicted since the physicochemical characteristics and the temporal positioning of the molecule in the skin are better understood and defined as opposed to those associated with an unlinked or un-bonded formulation containing the same two substances.

The efficiency and the focused application of use with the present invention includes the use of a broad class of novel molecules, containing at least two types of functional characteristics, including linking a vasodilator or a drug molecule to a molecule designed to promote penetration through the skin or to another type of vasodilator. The three classes of molecules: vasodilators, penetration enhancers and drugs may be linked as combinations of vasodilator to drug; vasodilator to penetration enhancer and penetration enhancer to drug.

DETAILED DESCRIPTION OF THE INVENTION

The invention describes the preparation of novel bifunctional function molecules, created from chemical agents known to participate in the promotion of transdermal drug delivery. In addition, the preparation of these bifunctional molecules may also be used for the enhanced delivery of one of the components of the delivery vehicle, to serve as an active agent to itself, such as a chemical vasodilator for the purpose of improving local tissue blood flow in medical conditions known to exhibit compromised blood flow.

The basic design of this class of novel molecules combines, through a covalent or other formal chemical linkage, the function chemical group of one of the classes described with the complimentary functional group or molecule on one of the other classes of chemicals.

The linkage of a penetration enhancer substance with either a vasodilator or a drug molecule endows this bifunctional molecule with superior dermal penetrating characteristics combined with an active vasodilation function or combined with the drug. By covalently binding these agents together as they are formulated and maintaining this bond as they pass through the stratum corneum and epidermis, both functional groups are co-migrating in the same physical space and also at the same time. The coordination of function and location in the skin tissue amplifies uptake of the drug or the delivery promoter, making the delivery vehicle more efficient and more substantial in effect.

The combinations of individual molecules, as defined by classes according to function, include but are not limited to chemical vasodilators, passive dermal penetration enhancing agents and drugs or diagnostic agents. The identification of a reaction chemical functional group available to serve as a linkage point to bond with a different functional class of molecule is critical to the selection of the specific molecules.

Examples of the chemicals available for selection for the chemical vasodilator class of molecules that are candidates to serve as one component of the bifunctional molecule, include, by example only but are not limited to: amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di-isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, xanthinol nicotinate, diazoxide, hydralazine, minoxidil, and sodium nitroprusside. Centrally acting agents include clonidine, quanaberz, and methyl dopa. Alpha-adrenoceptor blocking agents include indoramin, phenoxybenzamine, phentolamine, and prazosin. Adrenergic neuron blocking agents include bedmidine, debrisoquine, and guanethidine. ACE inhibitors include benazepril, captopril, cilazapril, enalapril, fosinopril, lisinopril, perindopril, quinapril, and ramipril. Ganglion-blocking agents include pentolinium and trimetaphan. Calcium channel blockers include amlodipine, diltiazem, felodipine, isradipine, nicardipine, nifedipine, nimodipine, and verapamil. Prostaglandins including: prostacyclin, thrombuxane A2, leukotrienes, PGA, PGA1, PGA2, PGE1, PGE2, PGD, PGG, and PGH. Angiotensin II analogs include saralasin. Other suitable vasodilators include nitroglycerin, labetalol, thrazide, isosorbide dinitrate, pentaerythritol tetranitrate, digitalis, hydralazine, diazoxide, and sodium nitroprusside. Typically the vasodilator linked to the penetration enhancer molecule, is present in the topical vehicle at concentration between 0.0005% to 15% by weight, depending on the specific vasodilator used and the pharmacologic properties of the chemical. When the vasodilator is linked to a drug molecule, similar concentrations are also used ranging from 0.0005% to 15% by weight, with the specific concentrations on a mole basis determined empirically by the bioavailability of the bifunctional molecule.

Another functional component of a bifunctional molecule is a dermal penetration enhancer. This class of molecules is designed to assist in the transportation of the bifunctional vasodilator molecule from the skin surface, through the stratum corneum and into the dermal layer of the skin. Suitable penetration enhancers include by example only but are not limited to: individual fatty acids, fatty acid esters, polyols, amides, various anionic, cationic and nonionic surfactants such as but not limited to sodium laurate and sodium lauryl sulfate, phospholipids, cholesterol and cholesterol derivatives, m-pyrrole, dimethyl acetamide, limonene, sphingolipids, ceramides, terpenes, alkanones, menthol, various organic acids, such as but not limited to salicylic acid, citric and succininc acid, prostaglandins, decyl methyl sulfoxide, urea, sulfoxide alcohols, plant extract oils. Suitable fatty acids include by example but are not limited to: linoleic acids, linolenic acids, oleic acids, stearic acids, and myristic acids. Phospholipids include by example but are not limited to: phosphatidylcholine, phosphatidylethanolamine, and phosphatidylserine. Plant extract oils include peanut oil, hemp, borage, olive oil, sunflower oil, soybean oil, monoi oil and macadamia oil, with olive oil being preferred. Suitable alcohols for the plant extract oil/alcohol mix include ethyl alcohol, isopropyl alcohol, methyl alcohol.

The third class of molecules that can be linked to either a vasodilator or a penetration enhancing molecule are therapeutic drugs and diagnostic agents. These drugs and agents include all small molecule, synthetic pharmaceuticals or diagnostic agents as well as bio-therapeutic agents, which are typically protein or peptides, but may be members of other classes of biological therapeutics, such as a lipid, carbohydrate or nucleic acid such as but not limited to insulin, antisense oligonucleotides, lipopolysaccahrides, human growth hormone and erythropoietin. The common element for linkage of vasodilators or penetration enhancer molecules to each of these small synthetic molecules or the biological therapeutics is that they all have functional chemical groups, such as free and chemically reactive carboxylic acid or amine groups available for reacting with and forming a bifunctional molecule with various penetration enhancer and/or vasodilator molecules. In addition to the functional groups on the therapeutic or diagnostic agents being available chemically, the attachment of the vasodilator or penetration enhancer needs to be either a chemically labile bond which may be cleaved upon entry into the body or a specific tissue or it needs to be physically positioned on the drug or diagnostic molecule such that the function of the drug or diagnostic agent is not impaired. The satisfaction of this point needs to be evaluated in a bioassay to determine the drug or diagnostic agent activity before and after the delivery to the body.

Examples of active ingredients that can be used in accordance with the present invention include, but are not limited to: acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, betamethasone, budesonide, bumetanide, butorphanol, carbamazepine, carphenazine, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, human growth hormone, hydralazine, hydrochlorothiazide, ibuprofen, indomethacin, insulin, isoproterenol, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, paramethasone, peptide fragments, perphenazine, phenylpropanolamine, probenecid, quinethazone, ritodrine, scopolamine, serotonin, terbutaline, terfenadine, tocamide, triamterine, trimethoprim, and valacyclovir.

In accordance with certain embodiments, one of the vasodilator, the penetration enhancer, or the drug molecule must have a functional group capable of reacting with a vasodilator, the penetration enhancer, or the drug molecule to form the bifunctional molecule. One suitable functional group is an acid halide. The following procedure is the preferred synthetic procedure to convert either: vasodilators, penetration enhancers or drug molecules which contain an acid functional group to acid halide intermediates, such as acid chlorides, to allow the intermediate to serve as a reactant for subsequent reactions in the development of bifunctional molecules:

As an exemplary procedure to employ for the creation of bifunctional molecules between the different groups of vasodilators, penetration enhancers, and drug molecules, the first step in this process when the first molecule contains an acid functional group, is converted to an acid halide, such as an acid chloride. The following procedure outlines the generalized procedure for this purpose:

To a stirring mixture of a carboxylic acid-containing molecule (1 mmol), pyridine (1.2 mmol) in 20 ml of dichloromethane at 0° C. was added oxylyl chloride (1.2 mmol) and 1 drop of anhydrous N,N-dimethylforman. The mixture was then warmed to room temperature gradually, and the stirring was continued for an additional 2 hrs. The resulting mixture was evaporated to dryness, forming an acid halide. The acid halide residue was re-dissolved in 5 ml of anhydrous pyridine. 1 mmol of ROH or R'NH$_2$ was then introduced to the mixture and stirred at room temperature overnight. The reaction mixture was diluted with 50 ml of ethyl acetate, washed with 20 ml of 1.0M Na$_2$CO$_3$ aqueous solutions, and dried over anhydrous MgSO$_4$. After concentration, the crude product was purified by flash column chromatograph on silica gel. The result the synthesis of a bifunctional molecule between the first molecule containing a carboxylic acid group with the second molecule, containing a free hydroxyl or amino group.

The starting materials used for the preparation of the bifunctional molecules with the vasodilators or drugs or penetration enhancing chemicals listed by example or by inference either naturally possesses the needed chemically reactive groups for the combination of the chemicals, or may be modified to possess the needed chemically reactive groups. In some instances, there may be a need or desire to prepare the starting chemical in such a way to create a more highly reactive chemical or a specifically reactive chemical with the design to optimize the combination to form the bifunctional or to direct the bifunctionalization in such a way to retain or maintain the desired functionality of the bifunctionalized molecule once the combination has been completed.

The following exemplify the preparation of bifunctional molecules in accordance with certain embodiments.

1a) Bifunctional Molecule formation between a penetration enhancer containing a hydroxyl group and a vasodilator containing a carboxylic acid group. Preparation of analogs of menthol, as an example of a penetration enhancer molecule containing a hydroxyl group with a vasodilator chemical containing a carboxylic acid functional group such as nicotinic acid:

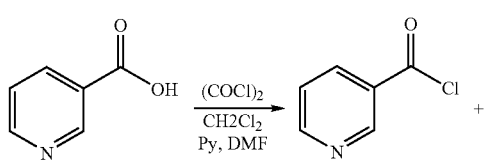

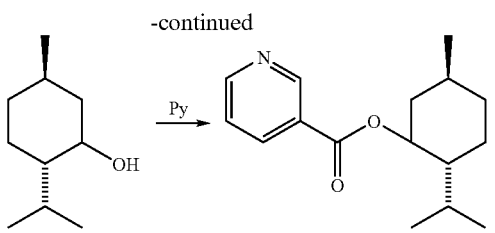

To a stirring solution of Nicotinic Acid (1 mmol) in 10 ml of dichloromethane at 0° C., was added oxylyl chloride (1.1 mmol) and 5 µl of anhydrous N,N-dimethylforamide (DMF). The resulting solution was warmed slowly to room temperature and the stirring was continued for additional 2 hrs until no gas was evolved. After evaporation of the solvent at reduced pressure, the residue was re-dissolved in 5 ml of anhydrous pyridine. 1 mmol of menthol was then added into the mixture and stirred at room temperature overnight. The reaction mixture was diluted with 50 ml of ethyl acetate, washed with 20 ml of 1.0M $Na_2CO_3$ aqueous solutions, and dried over anhydrous $MgSO_4$. After concentration, the crude product was purified by flash column chromatograph on silica gel. The result was the creation of a bifunctional molecule between the vasodilator nicotinic acid and the penetration enhancer menthol.

1b) Bifunctional Molecule formation between a penetration enhancer containing a carboxylic acid group and a vasodilator molecule containing an amine group. Preparation of analogs of oleic acid, as an example of a penetration enhancer molecule containing a carboxylic acid group with a vasodilator with a reactive amine group such as tolazoline:

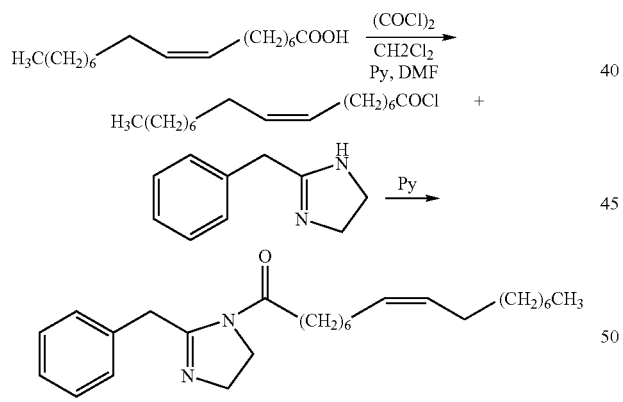

To a stirring solution of Oleic Acid (1 mmol) in 10 ml of dichloromethane at 0° C., was added oxylyl chloride (1.1 mmol) and 5 µl of anhydrous N,N-dimethylforamide (DMF). The resulting solution was warmed slowly to room temperature and the stirring was continued for additional 2 hrs until no gas was evolved. After evaporation of the solvent at reduced pressure, the residue was re-dissolved in 5 ml of anhydrous pyridine. 1 mmol of Tolazoline was then added into the mixture and stirred at room temperature overnight. The reaction mixture was diluted with 50 ml of ethyl acetate, washed with 20 ml of 1.0M $Na_2CO_3$ aqueous solutions, and dried over anhydrous $MgSO_4$. After concentration, the crude product was purified by flash column chromatograph on silica gel.

The result was the formation of a bifunctional molecule containing the vasodilator tolazoline and the penetration enhancer oleic acid.

2) Examples of bifunctional molecules prepared combining different chemical classes of passive penetration enhancing molecules reacted with different types of drugs containing different types of functional groups:

2a) Bifunctional Molecule formation between a therapeutic drug molecule containing a carboxylic acid group and a penetration enhancer molecule containing a free hydroxyl group. Preparation of analogs of ibuprofen, as an example of a drug containing reactive carboxylic acid groups with a penetration enhancer with a free alcohol group such as menthol:

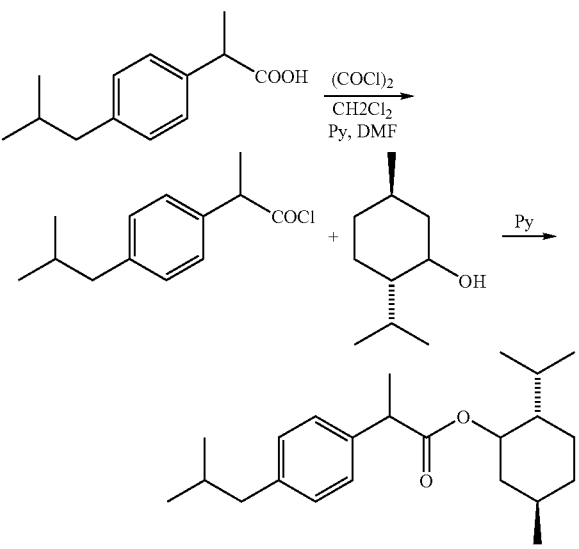

To a stirring solution of Ibuprofen (1 mmol) in 10 ml of dichloromethane at 0° C., was added oxylyl chloride (1.1 mmol) and 5 µl of anhydrous N,N-dimethylforamide (DMF). The resulting solution was warmed up slowly to room temperature and the stirring was continued for additional 2 hrs until no gas was evolved. After evaporation of the solvent at reduced pressure, the residue was re-dissolved in 5 ml of anhydrous pyridine. 1 mmol of menthol was then added into the mixture and stirred at room temperature overnight. The reaction mixture was diluted with 50 ml of ethyl acetate, washed with 20 ml of 1.0M $Na_2CO_3$ aqueous solutions, and dried over anhydrous $MgSO_4$. After concentration, the crude product was purified by flash column chromatograph on silica gel. The result was the creation of a bifunctional molecule containing the active drug molecule ibuprofen and the penetration enhancer menthol.

2b) Bifunctional Molecule formation between active drug molecules containing an amine group and penetration enhancer molecules containing a carboxylic acid group. Preparation of Analogs of Thiabendazole, as an Example of a Drug Containing Amine reactive groups with a penetration enhancer with a free carboxylic acid group such as oleic acid:

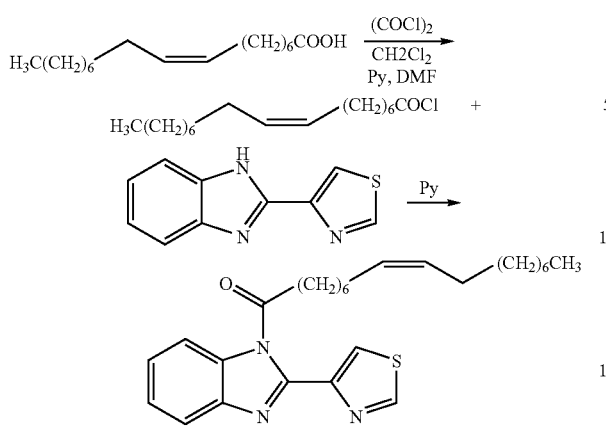

To a stirring solution of Oleic Acid (1 mmol) in 10 ml of dichloromethane at 0° C., was added oxylyl chloride (1.1 mmol) and 5 μl of anhydrous N,N-dimethylforamide (DMF). The resulting solution was warmed up slowly to room temperature and the stirring was continued for additional 2 hrs until no gas was evolved. After evaporation of the solvent at reduced pressure, the residue was re-dissolved in 5 ml of anhydrous pyridine. 1 mmol of thiabendazole was then added into the mixture and stirred at room temperature overnight. The reaction mixture was diluted with 50 ml of ethyl acetate, washed with 20 ml of 1.0M $Na_2CO_3$ aqueous solutions, and dried over anhydrous $MgSO_4$. After concentration, the crude product was purified by flash column chromatograph on silica gel. The result was the creation of a bifunctional molecule containing thiabendazole and oleic acid with the respective properties of both on one molecule for the purpose of delivery characteristics.

2c) Bifunctional Molecule formation between drug molecules an amine group with a penetration enhancer in the form of an acid halide intermediate. Preparation of clonidine analogs, as an example of a drug containing double, or single amine groups in combination with the chlorinated carboxylic acid intermediate of a passive dermal penetration enhancer such as linoleic acid.

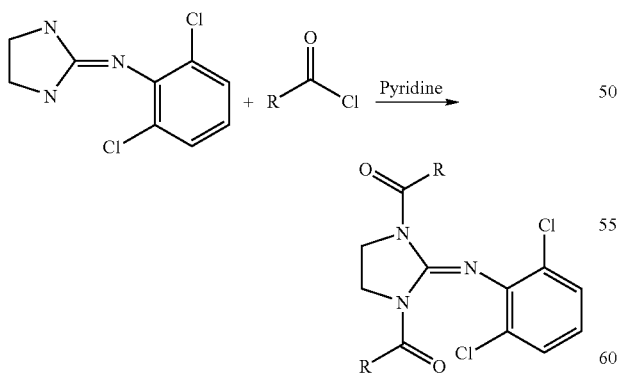

a. To a stirring solution of Oleic Acid (1 mmol) in 10 ml of dichloromethane at 0° C., was added oxylyl chloride (1.1 mmol) and 5 μl of anhydrous N,N-dimethylforamide (DMF). The resulting solution was warmed up slowly to room temperature and the stirring was continued for additional 2 hrs until no gas was evolved. The mixture was then evaporated to dryness.

b. To a stirring mixture of clonidine (1 mmol) in anhydrous pyridine (5~10 mL), was added the freshly prepared acid chloride (2 mmol).

c. The resulting mixture was then stirred at room temperature overnight, and the pyridine was then evaporated under reduced pressure.

d. The residue was re-dissolved in Ethyl Acetate or dichloromethane, and washed with water.

e. The organic layer was then dried over anhydrous Na2SO4. After concentration, the residue was purified by re-crystallization in appropriate solvent. The residue contains the bifunctional molecule composed of clonidine and linoleic acid.

Examples of acids=linoleic acid, linolenic acid, oleic acid, etc.

3) Examples of bifunctional molecules prepared combining different chemical classes of vasodilator molecules reacted with different types of drugs containing different types of functional groups:

3a) Preparation of analogs of thiabendazole as examples of drugs containing amine and sulfur groups linked with chlorinated intermediates of carboxylic acid containing vasodilators such as nicotinic acid:

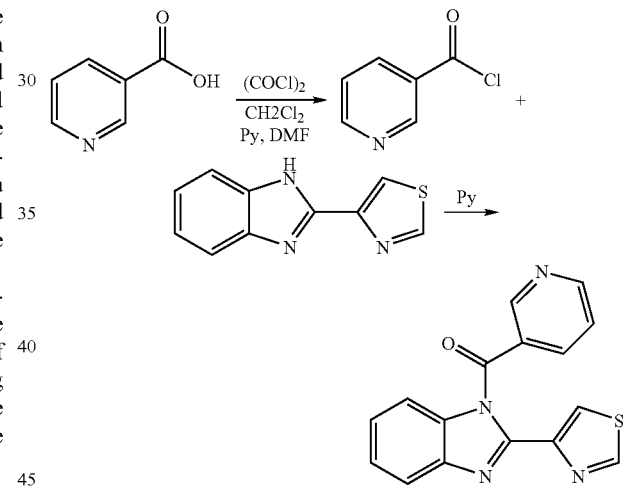

To a stirring solution of Nicotinic Acid (1 mmol) in 10 ml of dichloromethane at 0° C., was added oxylyl chloride (1.1 mmol) and 5 μl of anhydrous N,N-dimethylforamide (DMF). The resulting solution was warmed up slowly to room temperature and the stirring was continued for additional 2 hrs until no gas was evolved. After evaporation of the solvent at reduced pressure, the residue was re-dissolved in 5 ml of anhydrous pyridine. 1 mmol of thiabendazole was then added into the mixture and stirred at room temperature overnight. The reaction mixture was diluted with 50 ml of ethyl acetate, washed with 20 ml of 1.0M $Na_2CO_3$ aqueous solutions, and dried over anhydrous $MgSO_4$. After concentration, the crude product was purified by flash column chromatograph on silica gel. The result was the formation of a bifunctional molecule composed of thiabendazole and nicotinic acid.

3b) Preparation of methyldopa analogs as examples of drugs containing carboxyl, amine and alcohol groups with vasodilators containing carboxylic acids groups such as nicotinic acid:

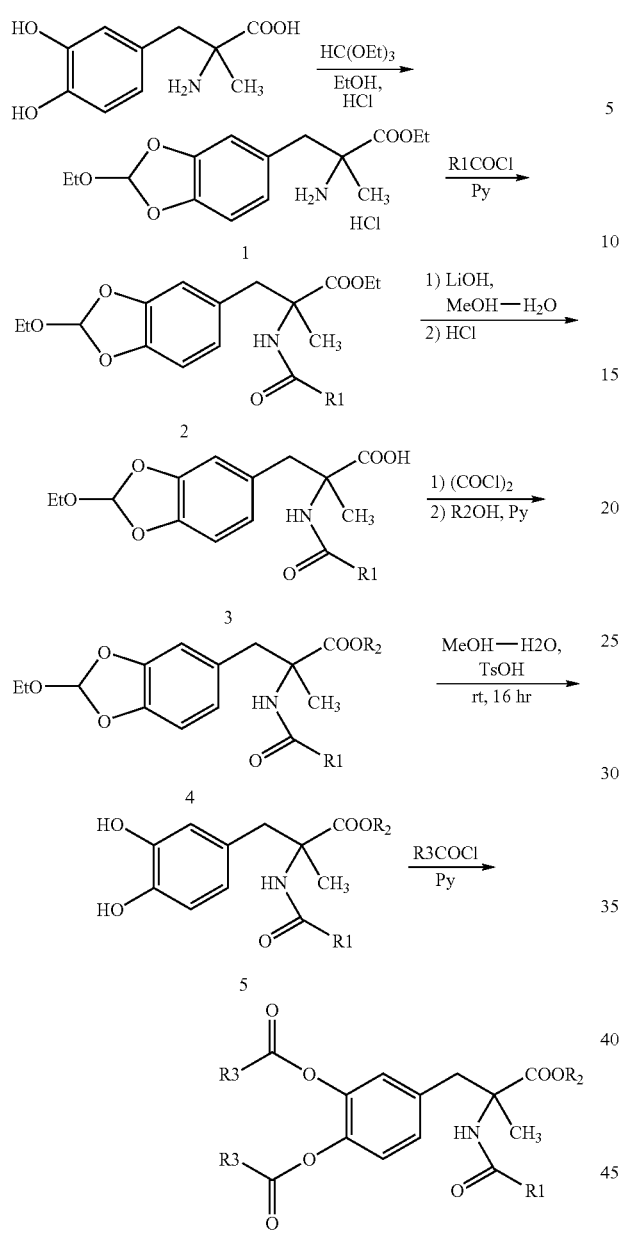

1. Method to convert an acid-containing active drug molecule such as methyldopa to an acid chloride: To a stirring solution of methyldopa acid (1 mmol) in 10 ml of dichloromethane at 0° C., was added oxylyl chloride (1.1 mmol) and 5 μl of anhydrous N,N-dimethylforamide (DMF). The resulting solution was warmed up slowly to room temperature and the stirring was continued for additional 2 hrs until no gas was evolved. The mixture was evaporated to dryness.
2. To the solution of methyldopa (1 equiv) in anhydrous ethanol, was added ethyl orthoformate (3 equiv) and HCl-dioxane (commercially available from Aldrich, 1.5 equiv). The resulting mixture was refluxed for 4 hrs, and evaporated under reduced pressure to yield compound 1.
3. Compound 1 was dissolved in anhydrous pyridine, and freshly prepared acid chloride according step 1 (1.1 equiv) was added. The resulting solution was stirred at room temperature overnight, and the pyridine was then evaporated under reduced pressure. The residue was re-dissolved in ethyl acetate or dichloromethane, and washed with water. The organic layer was then dried over anhydrous $Na_2SO_4$. After concentration, the residue was purified by re-crystallization in appropriate solvent. The product is amide 2.
4. Amide 2 was dissolved in anhydrous MeOH, and 2.0 M aqueous LiOH (2.0 equiv) was added. The solution was stirred at room temperature for 2 hr, and neutralized with diluted HCl solution to pH=7. After evaporation, the residue was extracted using dichloromethane-H2O. The organic layer is dried and concentrated to give acid 3.
5. Acid 3 was converted to corresponding acid chloride using the same method in step 1. To the alcohol R2OH in pyridine, was added the corresponding acid chloride derived from acid 3. The resulting solution was stirred at room temperature overnight, and the pyridine was then evaporated under reduced pressure. The residue was re-dissolved in ethyl acetate or dichloromethane, and washed with water. The organic layer was then dried over anhydrous $Na_2SO_4$. After concentration, the residue was purified by re-crystallization in appropriate solvent. The product is ester 4.
6. Ester 4 was dissolved in MeOH—$H_2O$ (v/v 1/1), para-tosylsulfonic acid (0.1 equiv) was added. The resulting solution was stirred at room temperature overnight, and evaporated to dryness. The resulting catechol 5 was extracted using EtOAc—H2O, and re-crystallized in proper solvent,
7. R3COOH was first converted to the desired acid chloride using method in step 1.
8. To a solution of catechol 5 in pyridine, was added the acid chloride R3COCl. After overnight stirring, the pyridine was evaporated under reduced pressure. The residue was re-dissolved in ethyl acetate or dichloromethane, and washed with water. The organic layer was then dried over anhydrous $Na_2SO_4$. After concentration, the residue was purified by re-crystallization in appropriate solvent. The final product is bifunctional molecule composed of methyldopa and two different penetration enhancer components.
9. Examples of $R_1COOH$, $R_3COOH$=linoleic acid, linolenic acid, oleic acid.
10. $R_2OH$=menthol, $HO(CH_2)_5CH=CHCH_2CH=CHCH_2CH=CH(CH_2)_4CH$, $HO(CH_2)_7CH=CH(CH_2)_7CH3$ 3c) Ibuprofen reacted with the vasodilator tolazoline as an example of a drug containing a free carboxylic acid group combined with an amine-containing vasodilator:

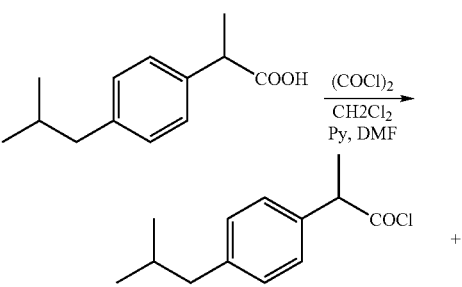

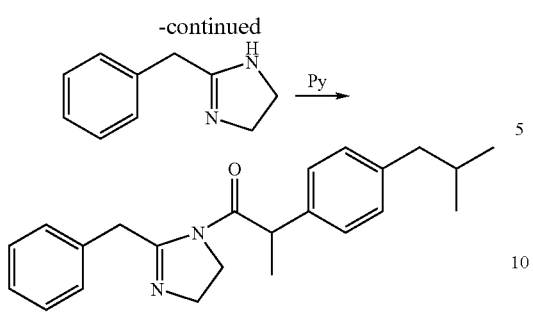

To a stirring solution of Ibuprofen (1 mmol) in 10 ml of dichloromethane at 0° C., was added oxylyl chloride (1.1 mmol) and 5 µl of anhydrous N,N-dimethylforamide (DMF). The resulting solution was warmed up slowly to room temperature and the stirring was continued for additional 2 hrs until no gas was evolved. After evaporation of the solvent at reduced pressure, the residue was re-dissolved in 5 ml of anhydrous pyridine. 1 mmol of tolazoline was then added into the mixture and stirred at room temperature overnight. The reaction mixture was diluted with 50 ml of ethyl acetate, washed with 20 ml of 1.0M $Na_2CO_3$ aqueous solutions, and dried over anhydrous $MgSO_4$. After concentration, the crude product was purified by flash column chromatograph on silica gel.

3d) Preparation of captopril-vasodilator bifunctional molecules, as examples of combining drugs containing both carboxyl and thiol groups with a chlorinated intermediate of a vasodilator such as nicotinic acid.

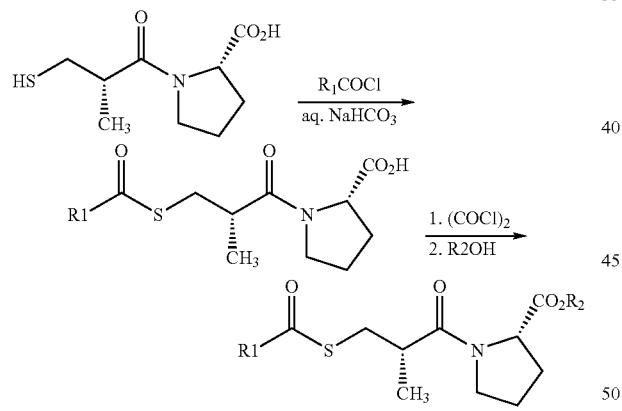

1) To a stirring solution of oleic acid (1 mmol) in 10 ml of dichloromethane at 0° C., was added oxylyl chloride (1.1 mmol) and 5 µl of anhydrous N,N-dimethylforamide (DMF). The resulting solution was warmed up slowly to room temperature and the stirring was continued for additional 2 hrs until no gas was evolved. The mixture was then evaporated to dryness.
2) With an ice bath, to the stirring suspension of captopril (1 equiv) in the mixed solvent of THF-10% aq. $NaHCO_3$ (v/v=3/1, $NaHCO_3$ 2 equiv) was added the freshly prepared acid chloride in step 1 (1.2 equiv).
3) The mixture was stirred at 0° C. for 1 hr, and 10° C. for 1 hr, and then extracted with EtOAc. The organic layer was separated, dried, and concentrated.
4) The resulting acid was converted to corresponding acid chloride using same procedure in step 1, and react with R2OH in pyridine.
5) The resulting solution was stirred at room temperature overnight, and the pyridine was then evaporated under reduced pressure. The residue was re-dissolved in ethyl acetate or dichloromethane, and washed with water. The organic layer was then dried over anhydrous $Na_sSO_4$. After concentration, the final product is obtained after flash column chromatography.

Examples of: $R_1COOH$=linoleic acid, linolenic Acid, oleic acid. $R_2OH$=menthol, $HO(CH_2)_5$ $CH=CHCH_2CH=CHCH_2CH=CH(CH_2)_4CH_3$, $HO(CH_2)_7CH=CH(CH_2)_7CH3$ 3e) Preparation of drugs containing reactive amine groups such as lisinopril and quinapril, with carboxylic acid containing vasodilators, such as nicotinic acid, the method used to prepare this novel class of analogs is identical to the method described in 3c.

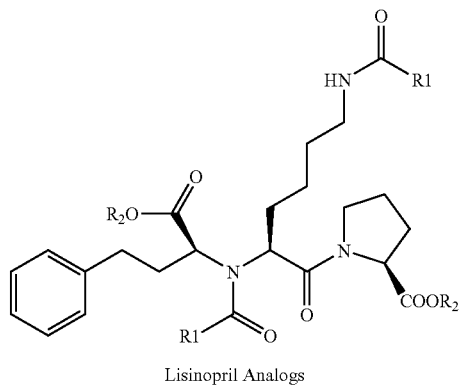

Lisinopril Analogs

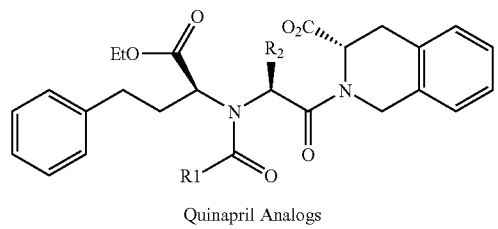

Quinapril Analogs

3f) Preparation of drugs containing both amine and alcohol groups such as phentolamine combined with vasodilators such as chlorinated intermediates of nicotinic acid.

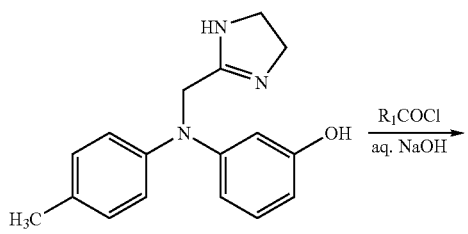

-continued

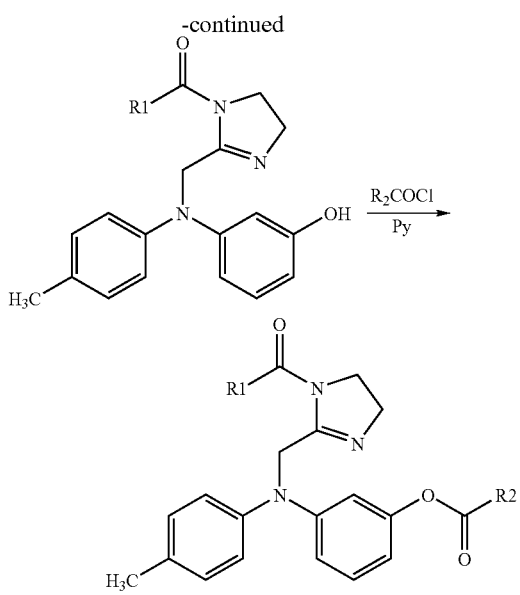

1) To a stirring solution of oleic acid (1 mmol) in 10 ml of dichloromethane at 0° C., was added oxylyl chloride (1.1 mmol) and 5 µl of anhydrous N,N-dimethylforamide (DMF). The resulting solution was warmed up slowly to room temperature and the stirring was continued for additional 2 hrs until no gas was evolved. The mixture was then evaporated to dryness.
2) With an ice bath, to the stirring suspension of phentolamine (1 equiv) in the mixed solvent of THF-10% aq. NaOH (v/v=3/1, NaOH 2 equiv) was added the freshly prepared acid chloride in step 1 (1.2 equiv).
3) The mixture was stirred and gradually warmed to room temperature for 2 hours.
4) The mixture was neutralized to pH=7 and extracted with EtOAc. The organic layer was separated, dried, and concentrated.
5) To a stirring solution of oleic acid (1 mmol) in 10 ml of dichloromethane at 0° C., was added oxylyl chloride (1.1 mmol) and 5 µl of anhydrous N,N-dimethylforamide (DMF). The resulting solution was warmed up slowly to room temperature and the stirring was continued for additional 2 hrs until no gas was evolved. The mixture was then evaporated to dryness.
6) The residue made in step 4 was dissolved in anhydrous pyridine, while freshly prepared acid chloride in step 5 was added slowly. After overnight stirring, the pyridine was evaporated under reduced pressure. The residue was re-dissolved in ethyl acetate or dichloromethane, and washed with water. The organic layer was then dried over anhydrous $Na_sSO_4$. After concentration, final product is obtained after flash column chromatography.

Examples of R1COOH, R2COOH=linoleic acid, oleic acid, linolenic acid.

The examples of the chemical entities, individually as well as the bifunctional combinations of those entities are listed and outlined above as examples only and are not limited to only those chemicals but rather to serve as examples of classes of molecules both in terms of functional group reactivity as well as in class of molecule.

Once the bifunctional functioning molecules have been synthesized, they may be incorporated as part of a topical or transdermal drug delivery vehicle, which may take the form of a solution, suspension, emulsion, lotion or cream or other pharmaceutical formulation designed to be applied to the skin surfaces. These formulations may be constructed as aqueous or anhydrous based formulations depending on the chemical nature of the active and the supporting components of the formulation to enable to these components to achieve maximum functionality as a result of the chemical compatibility of those ingredients with chemical composition of the formulation. For example, a water-soluble or compatible bifunctional molecule would be best suited to be prepared as part of a water-based formulation. In addition, these formulations may contain a lipid enriched composition to assist the complex to penetrate through the stratum corneum as well as preferred composition of a molecular occlusive barrier to promote the penetration and also to prevent the loss of water from the skin tissue.

Example 1 of a bifunctional molecule incorporated into a formulation composition as a lotion:
5% (w/w) Bifunctional molecule of a drug-vasodilator (i.e., ibuprofen-methyl nicotinate)
5% oleic acid
5% linolenic acid
3% propylene glycol
2% pemulen
2% lipomulse 165
1% cetyl alcohol
1% allantoin
76% distilled water The bifunctional molecule and allantoin are dissolved into the water for the formulation in one vessel. Once dissolved, then the propylene glycol and pemulen are added slowly while mixing vigorously. In a separate vessel, containing the oleic acid and linolenic acid, the oil is heated to 55° C. then the cetyl alcohol and lipomulse are added while mixing until melted. The oil phase is allowed to cool to 30° C. then added slowly while stirring the water phase and blended until a proper emulsion has been formed.

The bifunctional molecule may be delivered by directly applying the substance to the skin and allowing the penetration characteristics of the formulation to enhance the delivery of the material into the skin tissue. Alternatively, the formulations may also be administered with the assistance of an external apparatus such as but not limited to a sonophoretic or iontophoretic device, in a process designed to introduce the bifunctional complex and the drug or diagnostic molecule into the dermis.

Those skilled in the art will appreciate that the drug material used may serve a second function to the process, for example the drug may be the vasodilator and as such, the creation of a vasodilator linked to a penetration enhancer molecule may be the objective for cases that are focused on a clinical endpoint of improving localized blood flow.

What is claimed is:
1. A method for the preparation of a bifunctional functioning molecule, comprising providing a first molecule having one of vasodilatory or dermal penetration enhancing properties that has a first reactive group in the molecule selected from the group consisting of an amine, an alcohol, a carboxylic acid functional group, and a hydroxyl group, and reacting said first molecule with a second molecule having the other of vasodilatory or dermal penetration enhancing properties that has a second reactive group in the molecule reactive with said first reactive group, said second reactive group being selected from the group consisting of an amine, an alcohol, a carboxylic acid functional group, and a hydroxyl group.

2. A bifunctional molecule comprising
   a. a vasodilator selected from the group consisting of amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di-isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, xanthinol nicotinate, diazoxide, hydralazine, minoxidil, sodium nitroprusside, clonidine, quanaberz, methyl dopa, indoramin, phenoxybenzamine, phentolamine, prazosin, bedmidine, debrisoquine, guanethidine, benazepril, captopril, cilazapril, enalapril, fosinopril, lisinopril, perindopril, quinapril, ramipril, pentolinium, trimetaphan, amlodipine, diltiazem, felodipine, isradipine, nicardipine, nifedipine, nimodipine, verapamil, prostacyclin, thrombuxane A2, leukotrienes, PGA, PGA1, PGA2, PGE1, PGE2, PGD, PGG, PGH, saralasin, nitroglycerin, labetalol, thrazide, isosorbide dinitrate, pentaerythritol tetranitrate, digitalis, hydralazine, diazoxide, and sodium nitroprusside;
   b. a dermal penetration enhancer selected from the group consisting of linoleic acids, linolenic acids, oleic acids, stearic acids, and myristic acids; sodium laurate, sodium lauryl sulfate, phosphatidylcholine, phosphatidylethanolamine, phosphatidylserine, cholesterol, m-pyrrole, dimethyl acetamide, limonene, menthol, salicylic acid, citric acid, succininc acid, decyl methyl sulfoxide, urea, peanut oil, hemp, borage, olive oil, sunflower oil, soybean oil, monoi oil and macadamia oil;
   wherein said vasodilator and said dermal penetration enhancer are covalently linked.

3. A bifunctional molecule comprising
   a. a vasodilator selected from the group consisting of amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di-isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, xanthinol nicotinate, diazoxide, hydralazine, minoxidil, sodium nitroprusside, clonidine, quanaberz, methyl dopa, indoramin, phenoxybenzamine, phentolamine, prazosin, bedmidine, debrisoquine, guanethidine, benazepril, captopril, cilazapril, enalapril, fosinopril, lisinopril, perindopril, quinapril, ramipril, pentolinium, trimetaphan, amlodipine, diltiazem, felodipine, isradipine, nicardipine, nifedipine, nimodipine, verapamil, prostacyclin, thrombuxane A2, leukotrienes, PGA, PGA1, PGA2, PGE1, PGE2, PGD, PGG, PGH, saralasin, nitroglycerin, labetalol, thrazide, isosorbide dinitrate, pentaerythritol tetranitrate, digitalis, hydralazine, diazoxide, and sodium nitroprusside;
   b. an active drug molecule selected from the group consisting of acetaminophen, acetohydoxamic acid, acetophenazine, acyclovir, albuterol, allopurinol, amiloride, amoxicillin, amphetamine, ampicillin, atenolol, baclofen, beclomethasone, betamethasone, budesonide, bumetanide, butorphanol, carbamazepine, carphenazine, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, estradiol, fenoprofen, human growth hormone, hydralazine, hydrochlorothiazide, ibuprofen, indomethacin, insulin, isoproterenol, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, paramethasone, perphenazine, phenylpropanolamine, probenecid, quinethazone, ritodrine, scopolamine, serotonin, terbutaline, terfenadine, tocainide, triamterine, trimethoprim, and valacyclovir;
   wherein said vasodilator and said active drug molecule are covalently linked.

4. A bifunctional molecule comprising
   c. a. a dermal penetration enhancer selected from the group consisting of linoleic acids, linolenic acids, oleic acids, stearic acids, and myristic acids; sodium laurate, sodium lauryl sulfate, phosphatidylcholine, phosphatidylethanolamine, phosphatidylserine, cholesterol, m-pyrrole, dimethyl acetamide, limonene, menthol, salicylic acid, citric acid, succininc acid, decyl methyl sulfoxide, urea, peanut oil, hemp, borage, olive oil, sunflower oil, soybean oil, monoi oil and macadamia oil;
   b. an active drug molecule selected from the group consisting of acetaminophen, acetohydoxamic acid, acetophenazine, acyclovir, albuterol, allopurinol, amiloride, amoxicillin, amphetamine, ampicillin, atenolol, baclofen, beclomethasone, betamethasone, budesonide, bumetanide, butorphanol, carbamazepine, carphenazine, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietic, estradiol, fenoprofen, human growth hormone, hydralazine, hydrochlorothiazide, ibuprofen, indomethacin, insulin, isoproterenol, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, paramethasone, perphenazine, phenylpropanolamine, probenecid, quinethazone, ritodrine, scopolamine, serotonin, terbutaline, terfenadine, tocainide, triamterine, trimethoprim, and valacyclovir;
   wherein said dermal penetration enhancer and said active drug molecule are covalently linked.

* * * * *